United States Patent [19]

Bailey et al.

[11] Plant 5,123

[45] Oct. 18, 1983

[54] PEACH TREE - N.J. F-2 CULTIVAR

[75] Inventors: Catherine H. Bailey, Englishtown; L. Fredric Hough, Cream Ridge, both of N.J.

[73] Assignee: Stark Brothers Nurseries and Orchards Company, Louisiana, Mo.

[21] Appl. No.: 366,231

[22] Filed: Apr. 7, 1982

[51] Int. Cl.[3] ..... A01H 5/03

[52] U.S. Cl. ..... Plt./42

[58] Field of Search ..... Plt./42

*Primary Examiner*—Robert E. Bagwill

*Attorney, Agent, or Firm*—Burns, Doane, Swecker & Mathis

[57] ABSTRACT

A new and distinct peach variety which originated by the crossing of an unnamed New Jersey seedling No. 602903 with pollen from the Pallas variety is provided. The freestone fruit of the new variety has a highly blushed red skin and a distinctive configuration which is vertically compressed and oblate. The flesh is fine and tender and of mild and delicate flavor. The variety has exhibited resistance to common bacterial leaf spot, and the fruit buds have exhibited exceptionally good winter hardiness.

1 Drawing Figure

SUMMARY OF THE INVENTION

The new and distinct variety of peach tree originated through the hand pollination of an unnamed New Jersey seedling No. 602903 with pollen from the Pallas peach variety (non-patented). The resulting seed from these hand pollinated flowers was germinated in a greenhouse during the winter of 1962–1963 and planted out-of-doors during the spring of 1969 in Orchard Block C2 at the New Jersey Agriculture Experiment Station at Cream Ridge, New Jersey. Tree 178 of Row 6 of this block first fruited in the summer of 1971 and was selected because of its distinctive characteristics. This seedling was designated No. 682061070. Evaluation of this seedling continued and during the summer of 1977 trees of the new variety were asexually reproduced by budding and have been further observed.

Trees of the new variety have been found to exhibit:

(a) the abundant formation of highly blushed red skinned fruit having a distinctive vertically compressed oblate configuration and freestone white flesh of mild flavor,
(b) a vigorous and spreading growth habit,
(c) exceptional winter hardiness of the fruit buds, and
(d) improved tolerance to bacterial leaf spot.

The configuration of the fruit is one of the most distinguishing characteristics. More specifically, the fruit is of the "peento type" whereby the equatorial diameter is considerably larger than the distance between the poles and the fruit accordingly is flattened at the poles. As illustrated in the photograph, the vertically compressed fruit configuration lacks an apex on the basal end. If the seed were removed such as by pushing out with the finger, the remaining fruit would exhibit a shape generally resembling that of a doughnut.

The fruit was found to possess a tough skin and to exhibit white flesh which is fine, tender and melting with a mild, delicate, and very good flavor.

The new variety was found to be a regular bearer and its buds were observed to be capable of withstanding low winter temperatures even when the buds of other peach varieties in the area commonly were damaged. Also the new variety has exhibited resistance to common bacterial leaf spot (i.e. *Xanthomonas pruni*) even under conditions where other trees in the surrounding area were severely infected.

The asexual propagation of the new variety by budding beginning in 1977 has demonstrated that its combination of characteristics comes true to form and is established and transmitted through succeeding generations.

The new variety has been named the N.J. F-2 Cultivar.

The specimens described herein were grown and observed at Cream Ridge, N.J.

BRIEF DESCRIPTION OF THE PHOTOGRAPH

The accompanying photograph shows typical specimens of the fruit and foliage of the new variety as depicted in color as nearly true as it is reasonably possible to make the same in a color illustration of this character.

DETAILED DESCRIPTION OF NEW VARIETY

Dates of first and last pickings: July 25 to Aug. 5, 1981.

Tree: Large size; vigorous; spreading; hardy; very productive; regular bearer.

*Trunk.*—Stocky; medium.

*Branches.*—Stocky; medium. Lenticels — medium number; small.

*Leaves.*—Elongated; pointed to acutely pointed; medium to thick thickness; smooth. Length — approximately 7 to 7½ inches. Width — medium. Color — medium to dark green; Plate VI K-35 Ridgway's Color Standards. Margin — finely serrate. Petiole — medium long; medium thick. Glands — average number: 3; opposite; medium to large; reniform.

Flowers:

*Date of first bloom.*—Apr. 8, 1981.

*Date of last bloom.*—Apr. 11, 1981.

*Size.*—Large.

*Color.*—Pink.

*Hardiness.*—Flower buds are very resistant to cold damage.

Fruit:

*Maturity when described.*—Hard; under ripe; date — Aug. 5, 1981.

*Size.*—Variable. Transverse diameter — approximately $2\frac{1}{8}$ to $2\frac{1}{4}$ inches. Axial diameter — approximately $\frac{3}{4}$ to $1\frac{1}{8}$ inch.

*Form.*—Variable; very compressed; sides unequal.

*Suture.*—Very shallow; has a slightly marked depression beyond the pistil point.

*Ventral surface.*—Rounded; ridged; absence of lips.

*Cavity.*—Abrupt; whitish-green undercolor. Depth — approximately $\frac{1}{4}$ inch. Breadth — approximately $\frac{1}{2}$ inch.

*Base.*—Truncated; indented.

*Apex.*—Lacking; there is usually a scar where the apex normally would be present.

*Stem.*—Medium thick; stout.

*Skin.*—Tough with no tendency to break during a wet growing season. Color — highly blushed; Nopal red Plate I-3.0-4i Ridgway's Color Standards; moderate quantity of short down.

*Flesh.*—Color — white. Amygdalin — scant; wanting in juice. Texture — melting. Fibers — fine; tender. Ripens — fairly evenly. Flavor — mild; delicate. Aroma — pronounced. Eating quality — very good.

*Stone.*—Freestone; parts from flesh smoothly. Size — Length — approximately $\frac{3}{4}$ inch. Thickness — approximately $\frac{7}{8}$ inch. Form — oblate. Base — broad. Apex — none. Sides — unequal. Surface — irregularly furrowed throughout.

Use: Local market; dessert.

Keeping quality: Medium.

Resistance to insects: Medium.

Resistance to diseases: Good; is resistant to common bacterial leaf spot (i.e. *Xanthomonas pruni*).

Shipping quality: Medium; must accommodate unusual shape.

We claim:

1. A new and distinct variety of peach tree substantially as illustrated and described, characterized by (a) the abundant formation of highly blushed red skinned fruit having a distinctive vertically compressed oblate configuration and freestone white flesh of mild flavor, (b) a vigorous and spreading growth habit, (c) exceptional winter hardiness of the fruit buds, and (d) improved tolerance to bacterial leaf spot.

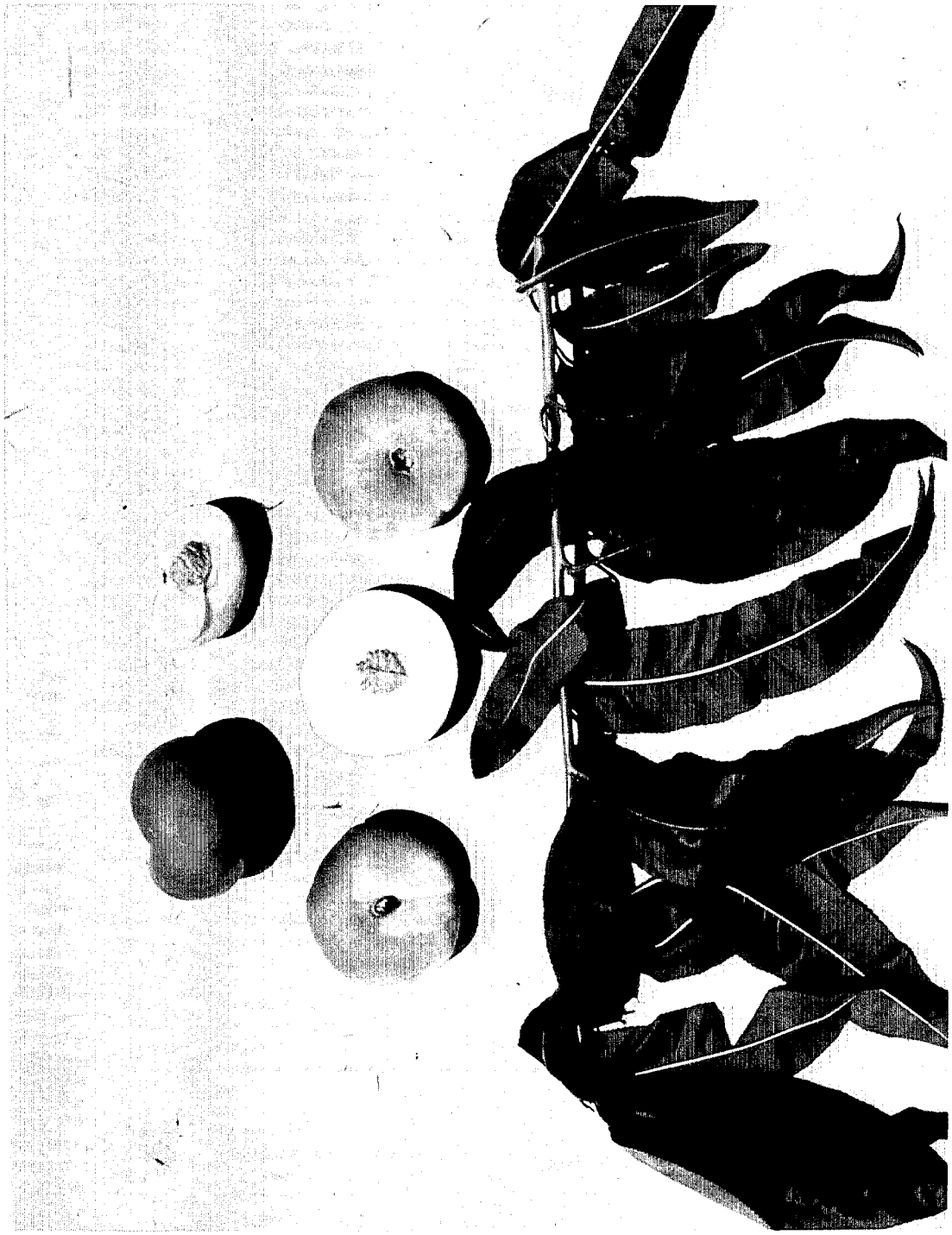

* * * * *